United States Patent [19]

Baker et al.

[11] 4,007,227
[45] Feb. 8, 1977

[54] CERTAIN OXIME COMPOSITIONS AND THEIR USE IN CONTROLLING FUNGI

[75] Inventors: Don R. Baker, Orinda; Arnold D. Gutman, Berkeley, both of Calif.

[73] Assignee: Stauffer Chemical Company, Westport, Conn.

[22] Filed: Feb. 28, 1975

[21] Appl. No.: 554,288

Related U.S. Application Data

[60] Division of Ser. No. 330,764, Feb. 8, 1973, Pat. No. 3,885,043, which is a continuation of Ser. No. 875,576, Nov. 10, 1969, abandoned.

[52] U.S. Cl. .................. 260/566 AE; 260/347.7; 260/465 E
[51] Int. Cl.² ............. C07C 131/02; C07C 131/04; C07C 131/06
[58] Field of Search .................. 260/566 AE, 465 E

[56] References Cited
UNITED STATES PATENTS 3,169,989  2/1965  Tieman et al. .............. 260/566 AE

OTHER PUBLICATIONS

Chem. Abstracts, vol. 58, Col. 8947(b), (1963).

Primary Examiner—Gerald A. Schwartz
Attorney, Agent, or Firm—Michael J. Bradley

[57] ABSTRACT

Compositions having the formula

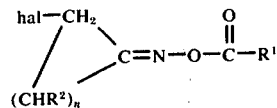

in which hal is chlorine, bromine or iodine, $R^1$ is (1) alkyl, (2) substituted alkyl, (3) alkenyl, (4) aryl, (5) nuclear substituted aryl in which the substituents are halogen, cyano, nitro, lower alkyl, or lower alkoxy, (6) styryl, (7) nuclear substituted styryl, in which the substituents are halogen, cyano, nitro, lower alkyl or lower alkoxy, (8) benzyl, (9) nuclear substituted benzyl in which said substituents are halogen, cyano, nitro, lower alkyl or lower alkoxy, (10) phenethyl, (11) nuclear substituted phenethyl in which the substituents are halogen, cyano, nitro, lower alkyl, or lower alkoxy, (12) cycloalkyl having 3 through 6 carbon atoms, (13) substituted cycloalkyl, and (14) furyl; $R^2$ is H, Cl, or lower alkyl; and $n$ is a whole number from 3 to 8, inclusive, and the use of these compositions as fungicides.

6 Claims, No Drawings

CERTAIN OXIME COMPOSITIONS AND THEIR USE IN CONTROLLING FUNGI

This is a division, of application Ser. No. 330,764 filed Feb. 8, 1973 now U.S. Pat. No. 5,885,043 which is a continuation of application Ser. No. 875,576 filed Nov. 10, 1969 now abandoned.

SUMMARY OF THE INVENTION

This invention relates to novel chemical compositions and to their use as fungicides. More particularly, the compositions of the present invention are those having the formula

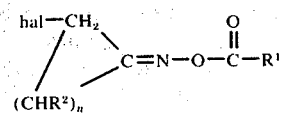

in which hal is a member selected from the group consisting of chlorine, bromine and iodine, $R^1$ is a member selected from the group consisting of (1) alkyl, (2) substituted alkyl in which the substituents are selected from the group consisting of halogen, nitro, and cyano, (3) alkenyl, (4) aryl, (5) nuclear substituted aryl in which the substituents are selected from the group consisting of lower alkyl, halogen, cyano, nitro, lower alkoxy, (6) styryl, (7) nuclear substituted styryl, in which the substituents are selected from the group consisting of halogen, cyano, nitro, lower alkyl and lower alkoxy, (8) benzyl, (9) nuclear substituted benzyl in which said substituents are selected from the group consisting of halogen, cyano, nitro, lower alkyl and lower alkoxy, having 1 through 4 carbon atoms, (10) phenethyl, (11) nuclear substituted phenethyl in which the substituents are selected from the group consisting of halogen, cyano, nitro, lower alkyl and lower alkoxy, (12) cycloalkyl having 3 through 6 carbon atoms, (13) substituted cycloalkyl having 3 through 9 carbon atoms, wherein the substituents are selected from the group consisting of halogen, cyano, nitro, alkyl of 1 through 3 carbon atoms, and alkoxy of 1 through 3 carbon atoms, (14) furyl, $R^2$ is selected from H, Cl, and lower alkyl having 1 through 4 carbon atoms, and $n$ is a whole number from 4 to 8, inclusive.

In its preferred form, the invention relates to compositions having the formula

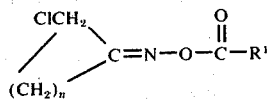

wherein $R^1$ is a member selected from the group consisting of alkyl of 1 through 10 carbon atoms, (2) substituted alkyl of 1 through 10 carbon atoms in which the substituents are selected from the group consisting of chlorine, bromine, nitro, cyano, (3) alkenyl of 1 through 10 carbon atoms, (4) phenyl, (5) nuclear substituted phenyl in which the substituents are selected from the group consisting of alkyl of 1 through 4 carbon atoms, chlorine, bromine, cyano, nitro, and alkoxy of 1 through 4 carbon atoms, (6) styryl, (7) nuclear substituted styryl in which the substituents are selected from the group consisting of chlorine, bromine, cyano, nitro, alkyl of 1 through 4 carbon atoms, alkoxy of 1 through 4 carbon atoms, (8) benzyl, (9) nuclear substituted benzyl in which the substituents are selected from the group consisting of chlorine, bromine, cyano, nitro, alkyl of 1 through 4 carbon atoms, alkoxy of 1 through 4 carbon atoms, (10) phenethyl, (11) nuclear substituted phenethyl in which the substituents are selected from the group consisting of chlorine, bromine, cyano, nitro, alkyl having 1 through 4 carbon atoms, alkoxy having 1 through 4 carbon atoms, (12) cycloalkyl of 4 through 6 carbon atoms, (13) substituted cycloalkyl having 4 through 9 carbon atoms wherein the substituents are selected from the group consisting of chlorine, bromine, cyano, nitro, alkyl having 1 through 3 carbon atoms, and alkoxy of 1 through 3 carbon atoms, (14) furyl, and n is a whole number from 4 to 8, inclusive.

The term "nuclear substituted" includes both mono and poly substitution with the specified substituent.

The term "halogen" or the prefix "halo" used in describing the compound of the present invention encompasses chlorine, bromine, iodine, and fluorine.

Representative compounds included in this invention are:

2-chlorocyclooctanone oxime bromoacetate
2-chlorocyclohexanone oxime methacrylate
2-chlorocyclohexanone oxime cyclohexane carboxylate
2-chlorocyclohexanone oxime chloroacetate
2-chlorocyclohexanone oxime cyclopropane carboxylate
2-chlorocyclohexanone oxime p-ethoxybenzoate
2-chlorocycloheptanone oxime p-methylbenzoate
2-chlorocyclohexanone oxime o-chlorocinnamate
2-chlorocyclohexanone oxime m-bromocinnamate
2-chlorocycloheptanone oxime benzoate
2-chlorocyclooctanone oxime p-methylbenzoate
2-chlorocyclohexanone oxime 3-chloropropionate
2-chlorocyclohexanone oxime crotonate
2-chlorocyclohexanone oxime 3-chlorobutyrate
2-chlorocyclohexanone oxime cyanoacetate
2-chlorocyclohexanone oxime 2,4-dichlorocinnamate
2-chlorocyclohexanone oxime 3,4-dimethoxycinnamate
2-chlorocyclohexanone oxime acrylate
2-chlorocyclohexanone oxime 3-ethoxypropionate
2-chlorocyclohexanone oxime isobutyrate
2-chlorocyclohexanone oxime benzoate
2-chlorocyclohexanone oxime m-nitrobenzoate
2-chlorocyclohexanone oxime sorbate
2-chlorocyclohexanone oxime 4-cyanobenzoate
2-chlorocycloheptanone oxime crotonate
2-chlorocyclohexanone oxime n-hexanoate
3(4)-methyl 2-chlorocyclohexanone oxime benzoate
2,3-dichlorocyclohexanone oxime benzoate
2-chlorocyclohexanone oxime p-chloro cinnamate
2-chlorocyclohexanone oxime bromoacetate
2-chlorocyclohexanone oxime p-chlorophenylacetate
2-chlorocyclohexanone oxime p-chlorobenzoate
2-chlorocyclohexanone oxime 2-furoate
2-chlorocyclohexanone oxime 1-naphthoate
2-chlorocyclohexanone oxime p-methoxy benzoate
2-chlorocyclohexanone oxime methoxyacetate
2-chlorocyclohexanone oxime p-methylphenylacetate
2-chlorocyclooctanone oxime benzoate
2-chlorocyclohexanone oxime p-nitrobenzoate
2-chlorocyclohexanone oxime trichloroacetate 2-chlorocyclohexanone oxime m-chlorobenzoate
2-chlorocyclohexanone oxime o-chlorobenzoate
2-chlorocycloheptanone oxime trichloroacetate
2-chlorocyclohexanone oxime p-cyanobenzoate
2-chlorocyclohexanone oxime p-iodobenzoate
2-chlorocycloheptanone oxime bromoacetate
2-chlorocyclohexanone oxime acetate
2-chlorocyclohexanone oxime p-methylbenzoate
2-chlorocyclohexanone oxime propionate
2-chlorocyclohexanone oxime butyrate
2-chlorocyclohexanone oxime propiolate
2,3-dichlorocyclohexanone oxime crotonate
2,3-dichlorocyclohexanone oxime acetate
2,3-dichlorocyclohexanone oxime propionate
2,3-dichlorocyclohexanone oxime acrylate
2-chlorocycloheptanone oxime p-methoxybenzoate The compositions of the present invention are particularly useful in inhibiting the growth of fungi. They may be prepared by reacting a compound of the formula

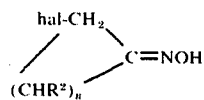

in which hal and $R^2$ are as defined before with a compound of the formula

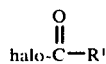

in which halo is chlorine or bromine and $R^1$ is a radical as defined as above. The concentrations of the reactants employed are not critical, although a slight excess of the acid halide may be employed.

The above reaction yields compounds of the formula

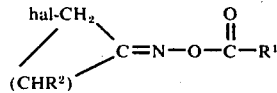

in which hal, $R^1$ and $R^2$ are defined as above.

The reactions are preferably carried out under anhydrous conditions in the presence of a base such as pyridine or triethylamine and in a solvent for the reactants. Suitable solvents include ether, benzene, chloroform or tetrahydrofuran. Reactions of this type are normally exothermic so that the addition of heat is not required. In actuality, cooling may sometimes be required to control the reaction rate. The reaction will normally be carried out at a temperature of from about 0° C. to about 55° C. Pressures may be atmospheric, sub-atmospheric, or greater than atmospheric, as desired.

EXAMPLE I

Preparation of 2-Chlorocyclohexanone Oxime Bromoacetate

Approximately 5.9 grams (0.04M) of 1-oximino-2-chlorocyclohexane is dissolved in 90 ml. of benzene and the solution is cooled to 10° C. About 8.1 gm. (0.04M) bromoacetyl bromide, diluted with 10 ml. of benzene, and 4.9 grams (6.7 ml.) of triethylamine are added dropwise simultaneously to the solution. Stirring is continued for 30 minutes and the mixture is allowed to come to room temperature. The mixture is then washed twice with water, twice with a mild $NaHCO_3$ solution, and again with water. The mixture is then dried over $MgSO_4$, and the solvent is evaporated to give the product 2-chlorocyclohexanone oxime bromoacetate.

EXAMPLE II

Preparation of 2-Chlorocycloheptanone Oxime Benzoate

Approximately 9.8 grams (0.06M) of 1-oximino-2-chlorocycloheptanone and 8.4 grams (0.06M) of benzoyl chloride is combined in 140 ml. of benzene and cooled to 10° C. Triethylene (6.2 grams) is added slowly, keeping the temperature between 15° C. and 20° C. The mixture is stirred for 30 minutes and allowed to come to room temperature. The mixture is then washed twice with water, twice with a mild $NaHCO_3$ solution, and again with water. The mixture is dried over $MgSO_4$, and the solvent evaporated to give the product 2-chlorocycloheptanone oxime benzoate.

EXAMPLE III

Preparation of 2-Chlorocyclohexanone Oxime Benzoate

The procedure of Example II is repeated except that 7.4 grams (0.05M) of 1-oximino-2-chlorocyclohexane, 7.0 gm. (0.05M) of benzoyl chloride, 5.1 grams (0.051M) of triethylamine, and 130 ml. of benzene are employed.

The following is a table of compounds that may be prepared according to the procedure described hereto. Compound numbers are assigned to each compound and are used throughout the remainder of the application.

TABLE I

| Compound Number | hal | $R^2$ | n | $R^1$ |
|---|---|---|---|---|
| 1 | chloro | H | 4 | bromomethyl |
| 2 | chloro | H | 4 | phenyl |
| 3 | chloro | H | 4 | 4-chlorophenyl |
| 4 | chloro | H | 6 | bromomethyl |
| 5 | chloro | H | 6 | phenyl |
| 6 | chloro | H | 6 | 4-methylphenyl |
| 7 | chloro | H | 4 | 4-methylphenyl |
| 8 | chloro | H | 4 | 4-methoxyphenyl |
| 9 | chloro | H | 4 | methylvinyl |
| 10 | chloro | H | 4 | chloromethyl |
| 11 | chloro | H | 4 | vinyl |
| 12 | chloro | H | 4 | trichloromethyl |
| 13 | chloro | H | 5 | phenyl |
| 14 | chloro | H | 5 | methylvinyl |
| 15 | chloro | H | 5 | 4-methylphenyl |
| 16 | chloro | H | 5 | bromomethyl |
| 17 | chloro | H | 5 | trichloromethyl |
| 18 | chloro | H | 5 | 4-methoxyphenyl |

The following tests illustrate utility of the compounds in controlling fungi.

In vitro vial test. This test measures the fungicidal properties of a compound when in contact with a growing fungus. The test is conducted by partially filling two 1-ounce vials with malt broth. Next, the test compound is added to the vials at a certain concentration, expressed in parts per million, and mixed with the broth. A water suspension of spores of the desired fungi (one organism per vial) is added. The vials are then sealed and incubated for one week; at this time the vials are examined and the results recorded. Table II shows the results of various compounds tested by the in vitro vial test.

TABLE II

| Compound | Concentration (p.p.m.) which inhibited growth* Fungus | |
|---|---|---|
| | *Aspergillus niger* | *Penicillium italicum* |
| 1 | >50 | 50 |
| 2 | (1) | (5) |
| 3 | (.5) | 5 |
| 4 | 25 | 25 |
| 5 | (5) | >50 |
| 6 | (5) | >50 |
| 7 | (5) | (10) |
| 8 | (50) | (50) |
| 9 | (5) | (25) |
| 10 | >50 | >50 |
| 11 | (5) | 25 |
| 12 | >50 | >50 |
| 13 | (5) | (10) |
| 14 | 10 | (25) |
| 15 | (5) | (25) |
| 16 | >50 | (50) |
| 17 | >50 | >50 |
| 18 | (25) | >50 |

*( ) = partial control

As can be seen by the test results, the compounds of the present invention find particular utility as fungicides. Additionally, several of the compounds of the invention, such as 2-chlorohexanone oxime benzoate may be employed as a bactericide and algaecide. Several of the compounds of the invention, such as 2-chlorohexanone oxime trichloroacetate, exhibit herbicidal activity.

The compositions may be applied directly to the fungus or may be applied to a locus to be protected. In either event, it is of course necessary that the fungus receive an effective dosage or amount, i.e., an amount sufficient to kill or retard growth. The compositions may be applied to or in textiles, leather, paint, soaps, paper, wood, plastic, oil, and any other substances susceptible of growth of fungi.

The compositions are normally employed with a suitable carrier and may be applied as a dust, spray, drench or aerosol. The compositions thus may be applied in combination with solvents, diluents, various surface active agents (for example detergents, soaps or other emulsifying or wetting agents, surface active clays) carrier media, adhesives, spreading agents, humectants and the like. They may also be combined with other biologically active compositions, including other fungicides, bactericides, and algaecides, insecticides, growth stimulators, acaricides, herbicides, molluscicides, etc., as well as with fertilizers, soil modifiers, etc. The compositions of the invention may be used in combination with an inert carrier and a surface active or emulsifying agent, and may also be applied in combination with other biologically active materials, in conjunction with a carrier and a surface active or emulsifying agent. The solid and liquid formulations can be prepared by any of the conventional methods well-known by those skilled in the art. Since the amount of active agent required will vary according to the fungi treated, precise limits on the amounts employed cannot be given. Determination of the optimum effective concentration for a specific application is readily conducted by routine procedures, as will be apparent to those skilled in the art. As indicated, the amount applied in a given case will be effective amount, i.e., an amount sufficient to give the type of control desired.

Various changes and modifications may be made without departing from the spirit and the scope of the invention described herein, as will be apparent to those skilled in the art to which it pertains.

We claim:
1. A compound having the formula

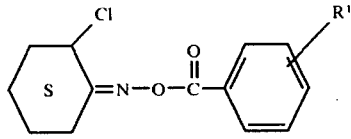

wherein R¹ is chlorine or bromine.

2. A compound having the formula

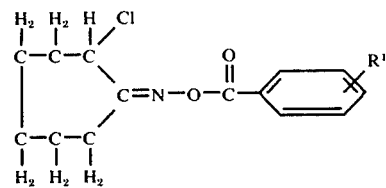

wherein R¹ is selected from the group consisting of 4-methylphenyl and 4-methoxyphenyl.

3. A compound having the formula

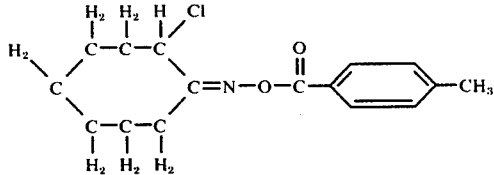

4. 2-chlorocyclooctanone oxime-p-chlorobenzoate.
5. 2-chlorocyclohexanone oxime-p-methoxybenzoate.
6. 2-chlorocycloheptanone oxime-p-methoxybenzoate.

* * * * *